US012214035B2

(12) United States Patent
Anderson et al.

(10) Patent No.: US 12,214,035 B2
(45) Date of Patent: Feb. 4, 2025

(54) HERPESVIRUS COMPOSITIONS AND RELATED METHODS

(71) Applicants: SANOFI PASTEUR LIMITED, Toronto (CA); SANOFI PASTEUR INC., Swiftwater, PA (US)

(72) Inventors: Stephen Anderson, Cambridge, MA (US); Simon Delagrave, Cambridge, MA (US); John Hamberger, Milford, NH (US); Qinglian Li, Aurora (CA); Sophia Mundle, Cambridge, MA (US); Nausheen Rahman, Toronto (CA)

(73) Assignees: SANOFI PASTEUR LIMITED, Toronto (CA); SANOFI PASTEUR INC., Swiftwater, PA (US)

( * ) Notice: Subject to any disclaimer, the term of this patent is extended or adjusted under 35 U.S.C. 154(b) by 388 days.

(21) Appl. No.: 17/576,021

(22) Filed: Jan. 14, 2022

(65) Prior Publication Data

US 2022/0133881 A1   May 5, 2022

Related U.S. Application Data

(62) Division of application No. 14/402,678, filed as application No. PCT/US2013/042039 on May 21, 2013, now Pat. No. 11,260,123.

(60) Provisional application No. 61/649,884, filed on May 21, 2012, provisional application No. 61/792,913, filed on Mar. 15, 2013.

(51) Int. Cl.
| | |
|---|---|
| *A61K 39/245* | (2006.01) |
| *A61K 9/00* | (2006.01) |
| *A61K 39/00* | (2006.01) |
| *A61K 39/12* | (2006.01) |
| *A61K 47/18* | (2017.01) |
| *A61K 47/26* | (2006.01) |
| *C12N 7/00* | (2006.01) |

(52) U.S. Cl.
CPC .......... *A61K 39/245* (2013.01); *A61K 9/0019* (2013.01); *A61K 39/12* (2013.01); *A61K 47/183* (2013.01); *A61K 47/26* (2013.01); *C12N 7/00* (2013.01); *A61K 2039/5254* (2013.01); *C12N 2710/16034* (2013.01); *C12N 2710/16611* (2013.01); *C12N 2710/16634* (2013.01); *C12N 2710/16651* (2013.01)

(58) Field of Classification Search
None
See application file for complete search history.

(56) References Cited

U.S. PATENT DOCUMENTS

| | | | |
|---|---|---|---|
| 4,337,242 A | 6/1982 | Markus et al. | |
| 4,338,335 A | 7/1982 | McAleer et al. | |
| 4,500,512 A | 2/1985 | Barme | |
| 5,024,836 A | 6/1991 | McAleer et al. | |
| 6,251,678 B1 | 6/2001 | Volkin et al. | |
| 6,258,362 B1 | 7/2001 | Loudon et al. | |
| 6,267,958 B1* | 7/2001 | Andya | A61K 38/16 424/155.1 |
| 6,267,967 B1 | 7/2001 | Johnston et al. | |
| 8,084,039 B2 | 12/2011 | Stinchcomb et al. | |
| 8,501,194 B2 | 8/2013 | Spector et al. | |
| 8,877,492 B2 | 11/2014 | Delagrave et al. | |
| 9,132,184 B2 | 9/2015 | Vellom et al. | |
| 9,365,832 B2 | 6/2016 | Mundle et al. | |
| 10,363,304 B2 | 7/2019 | Mundle et al. | |
| 2006/0141483 A1* | 6/2006 | Calton | A61K 39/245 435/5 |
| 2008/0248551 A1 | 10/2008 | Stinchcomb et al. | |
| 2008/0286850 A1 | 11/2008 | Liu et al. | |
| 2009/0325284 A1 | 12/2009 | Truran et al. | |
| 2010/0008944 A1 | 1/2010 | Knipe et al. | |
| 2010/0015180 A1 | 1/2010 | Francon et al. | |
| 2010/0247573 A1 | 9/2010 | Vellom et al. | |
| 2011/0201087 A1 | 8/2011 | Delagrave et al. | |
| 2016/0331832 A1 | 11/2016 | Mundle et al. | |

FOREIGN PATENT DOCUMENTS

| | | |
|---|---|---|
| EP | 0008255 | 2/1980 |
| EP | 0028563 | 5/1981 |
| EP | 0252059 | 1/1998 |
| EP | 2280064 A2 | 2/2011 |
| WO | 99/45104 A2 | 9/1999 |
| WO | 99/55348 | 11/1999 |
| WO | 2004/112707 A2 | 12/2004 |
| WO | 2008/057550 A2 | 5/2008 |

(Continued)

OTHER PUBLICATIONS

International Search Report dated Oct. 24, 2013 from International Application No. PCT/US2013/42039, pp. 1-12.
Hansen, Raino K. et al. Mechanisms of Inactivation of HSV-2 during Storage in Frozen and Lyophilized Forms. Biotechnol. Prog., 2005(21): 911-917.
Zhai, Suling et al. Effect of Freezing Rates and Excipients on the Infectivity of a Live Viral Vaccine during Lyophilization. Biotechnol. Prog., 2004(20): 1113-1120.
Extended European Search Report dated Dec. 16, 2015 for International Application No. EP13793902, 9 pages.
Apte et al., "Effect of Buffers and Stabilizers on Vaccine Stability and Efficacy", Development of Vaccines, Jan. 1, 2011, vol. 8, pp. 399-414.

(Continued)

*Primary Examiner* — Michelle S Horning
(74) *Attorney, Agent, or Firm* — MH2 Technology Law Group, LLP

(57) ABSTRACT

The present disclosure relates to liquid and dried compositions comprising a live, attenuated or genetically modified herpesvirus and methods of preparing such compositions, in one aspect, the composition comprises at least two or more pharmaceutically acceptable excipients, at least one of which is histidine and at least one of which is a sugar or sugar alcohol. The compostions retain a sufficiently high infectious titre following storage or large-scale manufacturing steps, such as lyophilization.

16 Claims, No Drawings

(56) References Cited

FOREIGN PATENT DOCUMENTS

WO 2013/095965 A1 6/2013

OTHER PUBLICATIONS

Abdul-Fattah et al., "Drying-Induced Variations in Physico-Chemical Properties of Amorphous Pharmaceuticals and Their Impact on Stability II: Stability of a Vaccine", Pharmaceutical Research, Feb. 15, 2007, vol. 24, No. 4, pp. 715-727.
Chen et al., "Opportunities and challenges of developing thermostable vaccines", Expert Review of Vaccines, May 1, 2009, vol. 8, No. 5, pp. 547-557.
Hansen et al., "Mechanisms of Inactivation of HSV-2 during Storage in Frozen and Lyophilized Forms", Biotechnology Progress, Sep. 5, 2005, vol. 21, No. 3, pp. 911-917.
Communication pursuant to Article 94(3) EPC from European Patent Office dated Sep. 28, 2017 for European Application No. EP13793902.1, 7 pages.
International Search Report and Written Opinion dated Mar. 11, 2013 from International Application No. PCT/US2013/020780 (Authorized Officer, Lee W. Young), 7 pages.
Supplementary Partial European Search Report, issued Apr. 15, 2015 from corresponding European Application No. 13735764.6, 5 pages.
Hoshino, et al., "Protection from Herpes Simplex Virus (HSV)-2 Infection with Replication-Defective HSV-2 or Glycoprotein D2 Vaccines in HSV-1-Seropositive and HSV-1-Seronegative Guinea Pigs," J. Infectious Dis., vol. 200, No. 7, Oct. 1, 2009, pp. 1088-1095.
Mundle, et al., "High-Purity Preparation of HSV-2 Vaccine Candidate ACAM529 Is Immunogenic and Efficacious In Vivo," PLOS One, vol. 8, issue 2, Feb. 2013, e57224, pp. 1-10.
O'Keeffe, et al., "The Affinity Adsorptive Recovery of an Infectious Herpes Simplex Virus Vaccine," Biotechnology and Bioengineering, vol. 62, No. 5, Mar. 5, 1999, pp. 537-545.
Kyle Grant, "Production and Purification of Highly Replication Defective HSV-1 Based Gene Therapy Vectors", Doctoral Dissertation, University of Pittsburgh, published through the online, D-scholarship@Pitt repository in 2008 with limited access for 5 years, pp. 1-137.
Extended European Search Report (includes European Search Report and European Search Opinion), dated Oct. 19, 2017 for European Patent Application No. 17178956.3, 8 pages.
Jenson et al., "Comparison of various transport media for viability maintenance of herpes simplex virus, respiratory syncytial virus, and adenovirus", Diagnostic Microbiology and Infectious Disease, Jul. 1, 1994, vol. 19, No. 3, pp. 137-142.
Mundle et al., "Preparation of pure, high titer, pseudoinfectious Flavivirus particles by hollow fiber tangential flow filtration and anion exchange chromatography", Vaccine, Dec. 1, 2014, vol. xxx, pp. 1-6.
Final Office Action dated Mar. 27, 2018 for U.S. Appl. No. 15/155,951, 5 pages.
Non-Final Office Action dated Nov. 3, 2017 for U.S. Appl. No. 15/155,951, 6 pages.
Non-Final Office Action dated Aug. 14, 2015 for U.S. Appl. No. 14/369,844, 11 pages.
Brandau et al., "Thermal Stability of Vaccines", Journal of Pharmaceutical Sciences, 2003, vol. 92, vol. 2, pp. 218-231.
Frank Kofi Bedu-Addo, "Understanding Lyophilization Formulation Development", Pharmaceutical Technology, Lyophilization, 2004, pp. 20-18.
Da Costa et al., "Construction, Phenotypic Analysis, and Immunogenicity of a UL5/UL29 Double Deletion Mutant of Herpes Simplex Virus 2", Journal of Virology, 2000, vol. 74, No. 17, pp. 7963-7971.
Non-Final Office Action dated May 12, 2021 for U.S. Appl. No. 16/505,168, 12 pages.
Knop et al., "Bioreactor Production of Recombinant Herpes Simplex Virus Vectors", Biotechnology Progress, 2007, vol. 23, No. 3, pp. 715-721.
Zhu et al., "Mixed matrix membranes decorated with, In situ self-assembled polymeric nanoparticles driven by electrostatic interaction", Journal of Materials Chemistry, 2018, vol. 6, pp. 7859-7870.

* cited by examiner

HERPESVIRUS COMPOSITIONS AND RELATED METHODS

CROSS-REFERENCE TO RELATED APPLICATIONS

This application is a Continuation of U.S. application Ser. No. 14/402,678 (Allowed) filed 20 Nov. 2014, which is a U.S. National Stage Application of PCT/US2013/042039 filed 21 May 2013, which claims the benefit of, and relies on the filing date of, U.S. provisional patent application No. 61/649,884, filed 21 May 2012, and U.S. provisional patent application No. 61/792,913, filed 15 Mar. 2013, the entire disclosures of which are herein incorporated by reference.

FIELD OF THE DISCLOSURE

The present invention relates to compositions (e.g., pharmaceutical compositions) and more particularly, to herpesvirus compositions.

BACKGROUND OF THE DISCLOSURE

The Herpesviridae are a family of enveloped, double-stranded DNA viruses, a number of which cause disease in humans and/or animals. At least seven herpesviruses are associated with infection in humans, including herpes simplex virus type-1 (HSV-1), herpes simplex virus type-2 (HSV-2), varicella zoster virus (VZV), Epstein Barr virus (EBV), cytomegalovirus (CMV), human herpesvirus-6 (HHV-6) and human herpesvirus-7 (HHV-7). Diseases caused by herpesviruses in humans vary from mild to severe, and in some cases, infection is life-threatening.

Vaccines of various types have been proposed for herpesviruses and have included for example, isolated immunogens (e.g., inactivated whole virus particles, viral subunit proteins), live, attenuated virus, and genetically modified viral mutants (e.g., replication-defective viral mutant strains). Live, attenuated or genetically modified viruses do not induce the disease caused by the corresponding wild-type virus in animals or humans but are nonetheless, capable of inducing a specific immune response in such subjects. Replication-defective viral mutant viruses are specifically defective for viral functions that are essential for replication, Such viruses are propagated in complementary cell lines that express the missing viral proteins to allow viral replication. In normal cells, one or more steps in viral replication are blocked, such that normal gene expression within the infected cell is allowed whereas production of progeny virus is not.

The effectiveness of a live attenuated or genetically modified (e.g., replication-defective) viral vaccine is dependent on, for example, its ability to elicit the required immune response against the disease. Any factor which inactivates the virus can reduce the vaccine efficacy.

Live attenuated and genetically modified herpesviruses are particularly labile and as a result, maintaining viral infectivity in vaccines that include these viruses is often problematic. For example, aqueous compositions of some attenuated or replication-defective herpesviruses are thermally unstable under typical storage temperatures (e.g., ≥5° C.) as evidenced by significant drops in viral infectious titre. Many aqueous compositions of HSV, for example, experience significant titre loss when stored for as little of 24 hours at 2-8° C. (i.e., the target storage temperature for a number of vaccines). HSV-2, in particular, is known to be very unstable in a liquid formulation at 25° C., 2-8° C., or −20° C. Hansen et al., (2005) Biotechnol. Prog, 21:911-917. Such thermolability represents a serious problem for manufacturing, shipping and storage.

Attempts have been made to increase viral stability or increase retention of viral infectivity for example, by the addition of one or more additives and/or by lyophilization.

U.S. Pat. No. 5,024,836 (Merck & Co Inc: W J McAleer et al) describes a stable lyophilized live herpesvirus vaccine that comprises from about 0.5% to about 8% moisture, and claims a gas injected lyophilized live attenuated varicella virus vaccine which comprises 2% to 8% moisture.

U.S. Pat. No. 4,338,335 and EP 0028563 (Merck & Co Inc: W J McAleer et al) describe stabilizer for liquid vaccines, and stabilized liquid live viral vaccine containing live virus, partially hydrolyzed gelatin, a monosaccharide or disaccharide, a cell culture medium, L-glutamic acid, L-arginine and buffer to maintain pH at from about 6.0 to about 6.5.

EP 0008255 (Merck & Co. Inc.: W J McAleer et al) describes a herpesvirus vaccine (particularly, a Marek's Disease vaccine) and its preparation. The virus is lyophilized in the presence of a pH controlled buffered stabilizer, so that the vaccine can be reconstituted with distilled water.

U.S. Pat. No. 6,258,362 (Loudon et. al.; Cantab Pharmaceuticals Research, Ltd.) describes stabilized lyophilized herpesvirus compositions that include a combination of vegetable peptone, buffer, and saccharide or sugar alcohol, or other mono- or oligo-saccharide or derivative thereof (e.g., lactose, sorbitol). As these formulations include peptone—an undefined mixture of peptides and other components—their use commercially may be problematic.

EP 0252059 (Smithkline Biologicals S.A.: ED'Hondt) describes stabilizers for attenuated vaccines, containing lactose, sorbitol, dextran, casein hydrolysate, L-glutamate, EDTA and buffer at a pH 6.7-7.2.

Zhai et al. (Biotechnol. Prog. 2004, 20, 1113-1120) describes lyophilized HSV formulations comprising sugar (i.e., trehalose, sucrose). Titre loss following lyophilization was significant however: formulations with sugar concentrations of 10% or less (e.g., 0.25%, 2%, 10% w/v trehalose; 5% w/v sucrose) had low viral titre recovery following lyophilization (e.g., 0.25% w/v trehalose had a viral recovery of about 22%). Viral titre recovery following lyophilization was higher for formulations including significantly higher concentrations of trehalose or sucrose (e.g., 27% w/v trehalose or sucrose) but was still less than optimal (e.g., 80% for 27% w/v trehalose, and less than 80% for 27% w/v sucrose). In addition, the long term stability of these formulations at various temperatures is questionable.

Formulations for other live, attenuated viruses are also known. U.S. Pat. No. 4,500,512 (Institut Pasteur, MBarne) describes stabilized lyophilized formulations for the yellow fever virus that include a combination, in phosphate buffered saline (PBS), of lactose, sorbitol, the divalent cations, calcium and magnesium, and at least one amino acid (selected from histidine, alanine, valine, threonine, arginine, methionine, hydroxyproline, lysine, isoleucine, phenylalanine and serine). U.S. Pat. No. 8,084,039 describes formulations for live attenuated viruses particularly for flaviviruses that include a combination, in phosphate buffered saline (PBS), of trehalose, copolymer poloxamer 407, Pluronic F127® and rHSA. Lyophilization, however, of PBS buffered formulations often results in significant changes to pH which is undesirable for labile herpesviruses.

These known methods have, nonetheless, failed to yield a live, attenuated or genetically modified herpesvirus composition that retains a sufficiently high titre or a production method suitable for large scale commercial manufacturing.

Thus, there remains a need for herpesvirus vaccines suitable for long term storage.

SUMMARY OF THE DISCLOSURE

The present disclosure relates to methods and compositions comprising an infectious herpesvirus and methods of preparing such compositions. In certain embodiments, the composition is stabilized such that following storage for 6 months at 5° C.±2° C., the composition retains an infectious titre within 0.25 $Log_{10}$ pfu/mL, 0.2 $Log_{10}$ pfu/mL, or even 0.1 $Log_{10}$ pfu/mL of the titre measured after the composition is dried. In another embodiment, following storage for 6 months at 25° C.±2° C., the dried composition retains an infectious titre within 0.5 $Log_{10}$ pfu/mL of the titre measured after the composition is dried.

One embodiment is directed to a composition comprising a live, attenuated or genetically modified herpesvirus, and at least two pharmaceutically acceptable excipients, at least one of which is histidine and at least one of which is a sugar or sugar alcohol. In one embodiment, the composition is a liquid composition. In one embodiment, the liquid composition remains stable following storage at 2-8° C. for up to 2 weeks. In another embodiment, the liquid composition remains stable following storage at 25° C.±2° C. for up to 1 week. In another embodiment, the composition is a dried composition. In one embodiment, the dried composition is stable following storage for at least 6 months at 5° C.±2° C. In another embodiment, the dried composition is stable following storage for at least 5 months at 25° C.±2° C.

The compositions, in certain embodiments, include a replication defective herpes simplex virus.

The compositions may be pharmaceutical compositions or vaccines. Kits including a first container containing the dried composition and a second container containing an aqueous solution for reconstitution the dried composition are also provided. Methods of preparing vaccines, for example, by reconstitution of the composition with an aqueous solution are also disclosed.

Other aspects provide methods of manufacturing such dried compositions. For example, one embodiment is directed to a method of manufacturing a dried composition comprising a live, attenuated or genetically modified herpesvirus, and at least two or more pharmaceutically acceptable excipients, at least one of which is histidine and at least one of which is a sugar or sugar alcohol, the method comprising: (i) admixing the live, attenuated herpesvirus with the at least two or more pharmaceutically acceptable excipients; and (ii) drying the admixture. In certain embodiments, the admixture is dried by means of freeze-drying, foam-drying or spray-drying. Advantageously, these dried compositions have an acceptable final dose target and shelf life.

DETAILED DESCRIPTION

The present disclosure provides compositions and methods that can be used as, or for the manufacture of, pharmaceutical products, including viral vaccines, as described further below. The compositions include pharmaceutically acceptable excipients that, as described further below, have been found to be advantageous in the preparation of stable herpesvirus vaccines that retain viral infectivity under desired storage conditions. The methods include steps, which involve drying that too has been found to be advantageous. These compositions and methods are described further below.

In one embodiment, compositions include a live, attenuated or genetically modified herpesvirus, and at least two pharmaceutically acceptable excipients, at least one of which is histidine and at least one of which is a sugar or sugar alcohol. In one embodiment, the composition is in a liquid form. The liquid compositions can be dried and stored for later use. Alternatively, the liquid compositions may be administered to a subject without being dried, Such liquid compositions can also be stored, in their liquid form, prior to administration. In addition, a dried form of the composition can be reconstituted using an aqueous solution such as, for example, water for injection, or a suitable diluent or buffer solution, to produce a liquid composition.

In another embodiment, the compositions are in a "dried" form which in the context of this disclosure refers to a product that has a residual moisture content of about 10% or less. Preferably, the residual moisture content is 0.5%-8.0% and, more preferably, the residual moisture content is 6% or less, 5% or less, 4% or less, or 3% or less. Methods of drying a composition are well known in the art, and include for example, but are not limited to freeze-drying, foam-drying and spray-drying. The compositions retain high infectious titre after being subjected to a drying process (e.g., freeze-drying) and also after storage for at least 6 months at 2-8° C.±2° C. (e.g., 5° C.±2° C.) or at higher temperatures (e.g., at 20-25° C.±2° C.).

Without intending to be bound by any theory, one or more of the pharmaceutically acceptable excipients included in the composition may contribute to viral stability (e.g., viral infectivity, integrity) by, for example, preventing or reducing viral inactivation and/or degradation. One measure of viral stability is viral infectivity which itself may be measured by assessing viral titre. Viral infectivity can be measured following one or more process steps in the manufacture of viral vaccine, such as following a drying (e.g., freeze-drying) step. Viral infectivity can also be measured after storage of the composition at sub zero, moderate (e.g., 5° C.±2° C.), or elevated temperatures (e.g., 25° C.±2° C.). One or more of the pharmaceutically acceptable excipients, including histidine and a sugar or sugar alcohol, may contribute individually or in combination to viral stability (e.g., viral integrity), For example, without intending to be bound by any theory, histidine may contribute to viral stability (e.g., viral integrity) and/or the maintenance of a particular pH level or range.

Histidine may be present in the composition at a concentration of about 1-50 mM, 5-20 mM (e.g., 5 mM) or 10 mM. While any suitable form of histidine may be used as is well known in the art, a preferred form is L-histidine.

Sugars that may be used in the compositions include, but are not limited to, non-reducing disaccharides (e.g., sucrose, trehalose). Sugar alcohols that may be used in the compositions include, but are not limited to, sorbitol and mannitol. In certain embodiments, the compositions include combinations of sugars and/or sugar alcohols. In one embodiment, the composition comprises sucrose and sorbitol. In another embodiment, the composition comprises sucrose. Sugars and/or sugar alcohols may be present at about 1-10% w/v or 10-20% w/v (e.g., 10%). In one embodiment, the composition includes sucrose at about 1-10% w/v, 1-15% w/v, or 10-20% w/v (e.g., 5% or 10%).

The composition may also include one more additional pharmaceutically acceptable excipients. Examples of use include but are not limited to buffers, salts, proteins (e.g., albumin), surfactants, bulking agents, chelating agents, gelling polymers, urea (or its derivatives), and combinations thereof.

Buffers that may be used in the compositions include for example, tris(hydroxymethyl)amino-methane (TRIS), TRIS-acetate, and HEPES (2-(4-(2-hydroxyethyl)-1-piperazinyl)ethanesulfonic acid). Buffer components such as TRIS, TRIS-acetate and HEPES may be present at a concentration of about 10-100 mM or 20-75 mM (e.g., 20 mM). In certain examples, compositions may include a mixture of buffer components. The compositions are generally of a pH of about, e.g., 6-9, 6.5-7.5, 6.5-7.0, 6.6, or 7.4. Preferably the pH is about 7.0 or 6.6.

Salts that may be used in the compositions include, for example, glutamate (e.g., potassium glutamate, mono sodium glutamate, sodium glutamate), sodium chloride, potassium chloride, and calcium chloride, in concentrations as is known in the art. Glutamate may, for example, be present at a concentration of about 10-100 mM, 25-75 mM (e.g., 25 mM) or 50 mM. Sodium chloride may, for example, be present at a concentration of about 10-100 mM, 100-200 mM, 80-160 mM (e.g., 80 mM, 160 mM). In certain examples, it may be preferable to include one or more salts. In one embodiment, compositions include potassium glutamate or sodium glutamate. In embodiments, compositions may also include sodium chloride.

In one embodiment, the composition comprises histidine and sucrose. In another embodiment, the composition comprises 5-20 mM histidine, 5-15% w/v sucrose or trehalose, 100-200 mM NaCl, and 25-75 mM potassium glutamate and has a pH of about 6.5 to 7.5. In yet another embodiment, the composition comprises 10 mM histidine, 10% w/v sucrose, 160 mM NaCl, 50 mM potassium glutamate, and has a pH of about 6.5 to 7.5, preferably about 7.0.

The composition may also include one or more surfactants and/or bulking agents. Surfactants of use include but are not limited poloxamers (e.g., Pluronic®), polysorbates (e.g., Tween® 80, Tween® 20), CTAB (hexadecyltrimethylammonium bromide), or SDS (sodium dodecyl sulfate or sodium lauryl sulfate). Bulking agents of use include but are not limited to PVP, PEG, dextran, mannitol and glycine.

The composition may also include urea (including urea derivatives such as e.g., thiourea, allylurea, acetamide, methylcarbamate or butylcarbamate) and/or albumin (e.g., BSA, rHSA). Gelling polymers may also be included such as, for example, gelatin, pectins, alginates, carrageenans and xanthan in concentrations as is known in the art. In certain examples, the stabilizer comprises gelatin.

Examples of herpesviruses suitable for use include, but are not limited to, Herpes Simplex virus type 1 (HSV-1) or type 2 (HSV-2), VZV, EBV, CMV, HHV-6, HHV-7 and the non-human equine herpesvirus type-1. Preferably, the virus is a live attenuated virus or a replication-defective virus. Live attenuated herpesviruses include: (i) viral vectors (e.g., that consist of a backbone herpesvirus, and in which certain genes have been replaced with that of another virus) and (ii) genetic mutants rendered nonvirulent by the deletion of one or more viral genes but retaining one or more viral glycoproteins, Examples of genetic mutants include replication defective HSV-1 or HSV-2 with mutations in the genes encoding ICP8, UL5 and/or ICP27, the HSV-2 mutant deficient in glycoprotein gH known as DISC and the HSV-2 mutant known as ICP10ΔPK). Examples of replication-defective herpesviruses suitable for use are provided, for example, in U.S. Pat. No. 7,223,411, which is incorporated herein in its entirety.

In one embodiment, the herpesvirus is a herpes simplex virus 2 (HSV-2). It is known in the art that HSV-2 is more thermolabile, and thus more difficult to stabilize, than HSV-1. Croughan, W. S., & Behbehani, A. M. (1988) *Journal of Clinical Microbiology*, 26(2):213-215. In addition, the HSV-529 virus is known to be very unstable in a liquid formulation at 25° C., 2-8° C., or −20° C. Hansen et al., (2005) Biotechnol. Prog. 21:911-917.

In certain embodiments, the herpesvirus is the replication-defective HSV-2 dl5-29 mutant virus (parent strain 186 syn+−1) genetically modified to contain 2 gene deletions: $U_L5$ and $U_L29$ as more fully described in Da Costa, et al (2000) J. Virology 74:7963-7971 and WO 99/06069, the disclosures of which are hereby incorporated by reference in their entirety. The original dl5-29 strain was re-derived and renamed as ACAM529 (Delagrave S, et al. PLoS ONE, 2012 7(10): e46714). Thus, the terms dl5-29, ACAM529, and HSV-529 are used interchangeably throughout this application. The UL5 deletion consists of removal of the UL5 gene and part of the nonessential UL4 open reading frame (ORF) from nucleotides 12,244 to 15,143. The UL5 gene is an essential component of the viral helicase-primase complex and is required for viral DNA synthesis. The UL29 deletion consists of removal of the complete UL29 gene from nucleotides 58,784 to 62,527. The UL29 gene encodes the viral single-stranded DNA binding protein ICP8 (infected cell protein 8), which is essential for viral DNA synthesis. Together, this double mutation results in a virus that only grows on a complementary cell line, AV529-19 Vero cells containing the UL29 and UL5 genes and does not grow on normal Vero cells.

In one embodiment, the herpesvirus (e.g. HSV-529) is highly purified and contains less than 10 ng host cell DNA per $1 \times 10^7$ PFU. Such highly purified herpesvirus can be purified using the methods described in PCT/US2013/020780, filed 9 Jan. 2013, which is incorporated herein by reference in its entirety.

In certain embodiments, compositions may comprise multiple herpesviruses (e.g., two, three or more herpesviruses) which may be of the same or different species. In some embodiments, compositions may comprise one or more virus serotypes (e.g., of HSV-1 and/or HSV-2).

In addition to viruses, the compositions may also include one or more peptides, proteins, or polysaccharide antigens optionally conjugated to carrier proteins. For example, compositions may include herpesvirus protein subunits (such as e.g., HSV glycoproteins gD and gB).

The attenuated herpesvirus may have been cultured on an appropriate cell line (e.g., Vero cells) and then purified from the harvested viral culture in one or more steps. A specific example of a cell line suitable for propagating a replication-defective HSV-2 strain is described in U.S. Pat. No. 6,841,373, which is incorporated herein in its entirety. In one embodiment, the herpesvirus is grown using serum-free media.

In one aspect, the liquid composition remains stable following storage at 2-8° C. For example, in one embodiment, the liquid composition has a titre loss of less than 0.3 $Log_{10}$ pfu/mL following storage at 2-8° C. for up to 2 weeks. In another embodiment, the liquid composition has a titre loss of less than 0.3 $Log_{10}$ pfu/mL following storage at 2-8° C. for 1-2 weeks. In another embodiment, the liquid composition has a titre loss of less than 0.3 $Log_{10}$ pfu/mL following storage at 2-8° C. for up to 1 week.

In another aspect, the liquid composition remains stable following storage at 25° C.±2° C. For example, in one embodiment, the liquid composition has a titre loss of less than 0.5 $Log_{10}$ pfu/mL following storage at 25° C.±2° C. for up to 1 week.

In yet another aspect, the liquid composition remains stable following storage at −70° C. For example, in one embodiment, the liquid composition has a titre loss of less than 0.1 $Log_{10}$ pfu/mL following storage at −70° C. for up to 38 weeks.

In another aspect, liquid composition remains stable following storage at −20° C. For example, in one embodiment, the liquid composition has a titre loss of less than 0.3 $Log_{10}$ pfu/mL following storage at −20° C. for up to 4 weeks.

In one embodiment, the compositions retain a high level of infectivity following the drying process (e.g., following freeze-drying). For example, in one embodiment, the composition retains an infectious titre of at least 75% or more following drying (e.g., following freeze-drying). In another embodiment, following drying (e.g., following freeze-drying), the composition retains an infectious titre within 0.75 $Log_1 a$ pfu/mL, 0.5 $Log_{10}$ pfu/mL, or 0.4 $Log_{10}$ pfu/mL of the titre measured before the composition is dried, when the viral titres in the liquid composition are between about $10^7$ to $10^5$ pfu/mL before drying.

In addition, dried compositions may optionally retain a high level of infectivity following extended storage at moderate or ambient temperatures. For example, in one embodiment, the composition retains an infectious titre of at least 75% following storage for at least one week at 10° C. or less (e.g., 2-8° C.±2° C.), In other embodiments, the composition retains an infectious titre of at least 75% following storage for at least 1 hour and up to 6 months or more at 25° C.±2° C. or less (e.g., 25° C.-20° C.; 2-8° C.). In certain embodiments, the composition retains: (i) an infectious titre of at least 80% following storage for at least one week at 10° C. or less; (ii) an infectious titre of at least 90% following storage for at least one week at 1000 or less; or (iii) an infectious titre of at least 95% following storage for at least one week at 10° C. or less.

In other embodiments, following storage for 6 months at 5° C.±2° C., the dried composition retains an infectious titre within 0.25 $Log_{10}$ pfu/mL of the titre measured after the composition is dried, when the viral titres in the liquid composition are between 10' to $10^5$ pfu/mL before drying. In certain embodiments, following storage for 6 months at 5° C.±2° C., the dried composition retains an infectious titre within 0.2 $Log_{10}$ pfu/mL of the titre measured after the composition is dried, when the viral titres in the liquid composition are between $10^7$ to $10^5$ pfu/mL before drying. In yet other embodiments, following storage for 6 months at 5° C.±2° C., the dried composition retains an infectious titre within 0.1 $Log_{10}$ pfu/mL of the titre measured after the composition is dried, when the viral titres in the liquid composition are between $10^7$ to $10^5$ pfu/mL before drying.

In other embodiments, following storage for 6 months at 25° C.±2° C., the dried composition retains an infectious titre within 0.5 $Log_{10}$ pfu/mL of the titre measured after the composition is dried, when the viral titres in the liquid composition range from $10^7$ to $10^5$ pfu/mL before drying.

The present disclosure also relates to a method of manufacturing a dried composition comprising a live attenuated or genetically modified herpesvirus and at least two pharmaceutically acceptable excipients, at least one of which is histidine and at least one of which is a sugar or sugar alcohol. In one embodiment, the method comprises (i) admixing the live, attenuated or genetically modified herpesvirus with at least two pharmaceutically acceptable excipients, at least one of which is histidine and at least one of which is a sugar or sugar alcohol; and (H) drying the admixture.

The admixture may be dried by means at any method known in the art. For example, the drying method may be selected from freeze-drying, foam-drying and spray-drying. The admixture may be dried to produce a dried composition having a residual moisture content of 10% or less, 6% or less, 5% or less, 4% or less, or 3% or less. Preferably, the admixture is dried to produce a dried composition having a residual moisture content of 0.5% to 8% (for example, as measured using a DL38 Karl Fisher Titrator). The resulting dried composition may be in the form of a solid (e.g., crystalline or amorphous) at 5° C., and at ambient temperature (e.g., 21° C. to at least 37° C.).

Manufacturing the compositions in this manner allows the preparation of a dried composition with a minimal reduction of titre loss during the drying process, and results in the preparation of compositions that retain sufficiently high titres under varying conditions of storage.

In certain embodiments, the composition is subjected to a freeze-drying process. Such a process can involve a freezing step, a primary drying (sublimation) step, and a secondary drying (desorption) step preferably for a total time of 48 hours or less.

The drying process may be completed in two steps: for example, in the first step, the aqueous composition may be frozen in the form of uniform particles or beads and in the second step, the frozen particles or beads may be dried so as to obtain a stabilized dried composition in the form of uniform particles or beads.

The total content of the components of the dried composition can be such that upon reconstitution with sterile liquid for injection (e.g., water for injection), the composition can be used to provide an injection which has an acceptable isotonic concentration (e.g., within a range of about 100-1100 mOsm, preferably within about 250-850 mOsm.

Also provided are methods of eliciting an immune response in a subject (e.g., a mammal) by administering the compositions to subjects. This may be achieved by the administration of the liquid compositions to the subject to effect exposure of the live, attenuated or genetically modified herpesvirus to the immune system of the subject.

The dose of virus can be chosen to be such as to yield in the reconstituted liquid for injection, a dose for example of about $10^3$ to about $10^8$ pfu virus. Typically, a volume of a dose for injection is about 0.5 mL. A preferred dose ranges from $1 \times 10^6$ to $5 \times 10^8$ pfu/dose. Dosages can be increased or decreased as to modulate immune response to be induced in a subject.

To prepare a vaccine for administration, a dried composition may be reconstituted with an aqueous solution such as, for example, water for injection, or a suitable diluent or buffer solution. In certain examples, the diluent includes histidine. The vaccine may be administered, in a suitable manner as is known in the art, such as for example, subcutaneously, intravenous, intramuscularly, intradermally, transcutaneously, transdermally or mucosally in amounts and in regimens determined to be appropriate by those skilled in the art. For the purposes of prophylaxis or therapy, the vaccine can be administered for example, 1, 2, 3 or 4 times. When multiple doses are administered, the doses can be separated from one another, by for example, one week, one month or several months (e.g., 3 months, 6 months).

Compositions (e.g. vaccines) may be used to prevent and/or treat herpesvirus infections. In one example, a composition comprising a live, attenuated or genetically modified HSV and a stabilizer may be used to prevent and/or treat HSV-1 and/or HSV-2 infection. In a preferred example, compositions comprising HSV-2 dl5-29 may be used to prevent and/or treat HSV-1 and/or HSV-2 and/or HSV-1 infection (e.g., genital HSV-2 infection). The prophylactic and therapeutic methods involve vaccination with the composition, for example, in preventing subsequent infection, or in carrying out the treatment itself.

The dried compositions may be included in a vaccine kit. For example, the kit may comprise a first container containing the dried composition and a second container containing an aqueous solution for reconstituting the composition. The kit may optionally include the device for administration of the reconstituted liquid form of the composition (e.g. hypodermic syringe, microneedle array) and/or instructions for use.

The following examples are provided for illustrative purposes only and are not intended to limit the scope of this disclosure in any way.

EXAMPLES

Example 1

The Examples included herein relate to a number of studies that were performed. The production and purification of the viral material utilized in those studies is described in this Example. The pharmaceutically acceptable excipients and the container closure system utilized in those studies are set out in Table 1.

TABLE 1

| Chemical Name | Vendor | CAS No | Grade |
|---|---|---|---|
| Sucrose | Sigma | 57-50-1 | BioUltra |
| Sorbitol | Sigma | SAP# 202082.5 | USP |
| MSG | Sigma | SAP#2000908 | USP |
| Urea | J. T Baker | 57-13-6 | USP |
| Glycine | J. T Baker | 56-40-6 | USP |
| Tris (Trizma Base) | Sigma | 77-86-1 | BioUltra |
| Tris Acetate (Trizma Acetate) | Sigma | 6850-28-8 | BioUltra |
| L-Histidine | J. T Baker | 71-00-1 | USP |
| Sodium Chloride | EM Science | 7647-14-5 | USP/EP |
| PVP | Sigma | 9003-39-8 | USP |
| Mannitol | J. T Baker | 69-65-8 | USP |
| Potassium Glutamate | Sigma | 6382-01-0 | N/A |
| Pluronic F68 | Sigma | 9003-11-6 | N/A |
| Dextran 40 | Sigma | 9004-54-0 | N/A |
| Albumin, Human Serum, Fraction V (rHSA) | Calbiochem | 70024-90-7 | Powder, purity >95% |
| Albumin, Bovine (BSA) | Sigma | 9048-46-8 | Purity >98% |
| Container closure system: | | | |
| 3 mL Type I borosilicate glass tubing vial | | BV0030 | |
| 13 mm Gray Chlorobutyl Serum Stopper (Latex free) | | SAP#: 3101821 | |
| Caps, 13 mm One Piece Aluminium Crimp Cap | | CS0001 | |

Viral Material

The replication-defective HSV-2 virus, dl5-29, re-derived and renamed ACAM529, was propagated on a large scale by growing the virus under serum free conditions on its complementing cell line AV529-19 (derived from Vero CCL-81.2 (African green monkey) cells). Liquid crude virus, purified frozen or lyophilized was used for infecting a monolayer of the complementing Vero cells. Following the growing period, the virus was harvested from cells and purified in a number of steps:

1. dislodging ACAM529 viral particles from surface of infected cells with a solution containing Dextran sulfate by exposing the cell culture to the solution for a sufficient period of time (e.g., 3 hours-24 hours),
2. Benzonase® endonuclease digestion of residual DNA in viral preparation,
3. clarification by depth filtration (e.g., using a 0.65 µm depth filter),
4. virus (bind-and-elute) purification by anion exchange chromatography, and
5. virus concentration/buffer exchange by tangential flow ultrafiltration/diafiltration (UF/DF).

An example of the production and purification process that may be utilized is described in co-International Patent Application PCT/US2013/020780, filed 9 Jan. 2013, which is incorporated herein by reference in its entirety.

The purified viral bulk was stored in storage buffer at about −70° C. For formulation, viral bulk was thawed in a water bath at 37° C.±2° C. Formulations were prepared for lyophilization as follows: (i) admixed applicable pharmaceutically acceptable excipients to prepare composition; (ii) added composition to bulk and admixed together until uniform; and (iii) aliquoted formulated bulk into vials and loaded vials into programmed freeze-dryer.

Example 2

The viral titre loss experienced by compositions of varying formulations: (i) as a consequence of lyophilization and (ii) following lyophilization, at certain temperatures for specific time periods were compared.

A number of studies were performed using aqueous compositions that were prepared under laminar flow conditions by admixing viral bulk material with one or more pharmaceutical excipients as discussed below. The pH of each composition was adjusted to the applicable pH level (as noted in Tables 4 and 5, ±0.2). Compositions were filtered through a 0.2 µM poly-vinyl di-fluoride disposable filter and then stored at 5° C. until lyophilization.

Following formulation, the aqueous compositions were freeze-dried (using FTS LYOSTAR® II). In brief, a dry state was achieved by freezing the aqueous composition and evaporating the resulting ice under vacuum through a sublimation process (without melting). The freeze-drying parameters were varied in each of studies A, B, C, D, and E. The freeze-drying cycle of Study A, B, and C was run substantially as summarized in Table 2 below.

TABLE 2

| Phases | Steps | Parameters | Study A (4x) | Study B | Study C* |
|---|---|---|---|---|---|
| Equilibrium | | Set Temp (° C.) | RT or 4 | 4 | −5 |
| | | Hold Time (min) | | 5 | 90 |
| Freezing | | Set Temp (° C.) | −45 | −50 | −50 |
| | | Ramp Rate (C./min) | 2.5 | 2.5 | 2.5 |
| | | Hold Time (min) | 180 | 180 | 180 |
| Primary Dry | A | Set Temp (° C.) | −35 | −35 | −35 |
| | | Ramp Rate (C./min) | 0.5 | 0.5 | 0.1 |
| | | Hold Time (min) | 600 | 600 | 600 |
| | | Vac (mTorr) | 45 | 45 | 45 |
| | B | Set Temp (° C.) | −20 | −20 | −25 |
| | | Ramp Rate (C./min) | 0.5 | 0.5 | 0.1 |
| | | Hold Time (min) | 480 | 480 | 600 |
| | | Vac (mTorr) | 45 | 45 | 45 |

TABLE 2-continued

| Phases | Steps | Parameters | Study A (4x) | Study B | Study C* |
|---|---|---|---|---|---|
| | C | Set Temp (° C.) | | | −15 |
| | | Ramp Rate (° C./min) | | | 0.1 |
| | | Hold Time (min) | | | 600 |
| | | Vac (mTorr) | | | 75 |
| Secondary Dry | | Set Temp (° C.) | 40 | 20 | 40 |
| | | Ramp Rate (° C./min) | 0.5 | 0.5 | 0.5 |
| | | Hold Time (min) | 400 | 1320 | 400 |
| | | Vac (mTorr) | 45 | 45 | 45 |

Certain physical parameters of each composition were evaluated, including, pH, osmolality and residual moisture. In a number of studies, the liquid glass transition temperature (Tg') and solid glass transition (Tg) was also assessed by testing liquid compositions (baseline before lyophilization) and lyophilized product by Conventional MDSC. A number of quality attributes were used to evaluate formulations, including the attributes set out in Table 3.

TABLE 3

| Attributes | Criteria |
|---|---|
| Cake Appearance | Pharmaceutical Elegant Cake |
| Residual Moisture | 0.5%-8.0%, more preferably, <3-5% |
| Reconstitution Time | <2 mins |
| pH | 6 to 8 |
| Osmolality | 250 to 900 osm/kg |
| Infectious Titre | Minimum loss during storage |
| Stability | Six (6) months or longer at 2-8° C. |

Viral infectious titre and activity of aqueous compositions before lyophilization (pre-lyo), following lyophilization (post-lyo) and following desired storage periods were measured using a plaque titration assay on the complementing Vero cell line to assess the stability of the different compositions. The assay was conducted substantially in the following manner: Tissue culture plates (12-well) were seeded one day prior to inoculation with $4\times10^5$ cells per well. Samples were serially diluted, plated and incubated 1 h, 37° C., 5% $CO_2$, with gentle rocking every 15 min. Methyl cellulose overlay medium (in DMEM supplemented with L-glutamine, heat-inactivated FBS and antibiotics) was added (1 mL) to each well and the plates were incubated 48 h. Plaques were visualized by staining with 1% crystal violet in 70% methanol. After manual counting of plaques, titers were represented as plaque forming units (PFU)/mL. The assay was assessed as having a standard deviation within the range of 0.04-0.16. The physical parameters and stability data for Studies A and B are set out in Table 4.

TABLE 4

Physical Parameters and Stability Data For Studies A and B

| Study | Composition | pH | Osmolality (mOsm) | Residual Moisture % | Pre-Lyo | Post-Lyo | Δ Lyo titre loss | 4 wk @ 5° C.*; 25° C.; 37° C. | 8 wk @ 5° C.* 25° C.; 37° C. | 12 wk @ −20° C.; 5° C.*; 25° C.; 37° C. | 26 wk @ −20° C.; 5° C.*, and 25° C. | Tg' (° C.) | Tg (° C.) |
|---|---|---|---|---|---|---|---|---|---|---|---|---|---|
| A(1) | 10% sucrose, 10% sorbitol, 1% monosodium glutamate, 2% PVP40, 2.4% glycine, 1.33% PVP40/20 mM Tris-acetate buffer pH 6.6 | 6.59 | 526 | 0.76 | 5.97 | 4.87 | 1.1 | 4.55** | n/a | n/a | n/a | n/a | 16.7 |
| A(1) | 5% sucrose & 2.6% Mannitol in 20 mM Tris-acetate pH 6.6 | 6.81 | 363 | 0.84 | 5.46 | 4.04 | 1.42 | 3.96** | n/a | n/a | n/a | −40.6 | 29.5 |
| A(1) | 5% sucrose & 2.5% Dextran (MW64000) 20 mM Tris-acetate pH 6.6 | 6.65 | 224 | 1.10 | 5.11 | 3.67 | 1.44 | 3.50** | n/a | n/a | n/a | −30.2 | 71.9 |
| A(1) | 5% PEG (mwt 8000) 20 mM Tris-acetate pH 6.6 | 9.53 | 57 | 1.16 | 5.79 | 0 | 5.79 | 0.00 | n/a | n/a | n/a | n/a | n/a |
| A(1) | 5% rHSA with 41 mM NaCl 20 mM Tris-acetate pH 6.6 | 7 | 105 | 2.06 | 5.81 | 3.4 | 2.41 | 3.16** | n/a | n/a | n/a | n/a | n/a |
| A(1) | 10% sucrose, 10% sorbitol, 1% monosodium glutamate, 2% PVP40, 2.4% glycine, 20 mM Tris-acetate pH 6.6 | 6.46 | 794 | 1.27 | 5.74 | 4.63 | 1.11 | 4.58** | n/a | n/a | n/a | n/a | 16.2 |
| A(1) | 10% sucrose, 10% sorbitol, 1% monosodium glutamate, 2% PVP40, 2.4% glycine, 10 mM Tris-HCl pH 7.4 | 7.36 | 918 | 1.33 | 6.36 | 5.74 | 0.62 | 5.30** | n/a | n/a | n/a | n/a | 13.2 |
| A(1) | 10 mM Histidine, 10% sucrose, 50 mM potassium glutamate, 160 mM NaCl, pH 7.0 | 7.02 | 858 | 4.87 | 7.38 | 6.48 | 0.9 | 6.38** | n/a | 6.24** | 6.13** | −41.9 | 30.6 |
| A(2) | 10% sucrose, 10% sorbitol, 1% monosodium glutamate, 2% PVP40, 2.4% glycine, Tris-Acetate pH 6.6 | 1.21 | 6.37 | 772 | 6.33 | 5.12 | 1.21 | 5.52** 5.32*** 5.24**** | n/a | n/a | n/a | −35.9 | 15.9 |

TABLE 4-continued

Physical Parameters and Stability Data For Studies A and B

| Study | Composition | pH | Osmolality (mOsm) | Residual Moisture % | Infectious Titre (log10 X/mL) | | | | | | Tg' (°C) | Tg (°C) |
|---|---|---|---|---|---|---|---|---|---|---|---|---|
| | | | | | Pre-Lyo | Post-Lyo | Δ Lyo titre loss | 4 wk @ 5° C.*; 25° C.; 37° C. | 8 wk @ 5° C.* 25° C.; 37° C. | 12 wk @ -20° C.; 5° C.*; 25° C.; 37° C. | 26 wk @ -20° C.; 5° C.*, and 25° C. | | |
| A(2) | 5% Suc w/ 0.5% MSG & 1% BSA | 6.13 | 475 | 1.26 | 7.94 | 6.42 | 1.52 | 5.29** | n/a | n/a | n/a | N/A | 51.0 |
| A(2) | 5% Suc w/ 0.5% MSG, 1% BSA & 1% PEG | 6.16 | 492 | 1.99 | 6.43 | 5.37 | 1.06 | 5.40** | n/a | n/a | n/a | N/A | 56.0 |
| A(2) | 5% Suc w/ 25 mM PG, 80 Mm NaCl, 10 mM Histidine | 7.00 | 449 | 1.41 | 6.55 | 5.83 | 0.72 | 6.04** | n/a | 5.64** | 5.47** | -41.9 | 26.2 |
| A(3) | 10% sucrose, 10% sorbitol, 1% monosodium glutamate, 2% PVP40, 2.4% glycine, 20 mM Tris Acetate pH 6.6 with 50 mM NaCl | 6.40 | 809 | 1.24 | 6.35 | 5.21 | 1.24 | 5.27** | 5.31** | n/a | n/a | -37.5 | 11.6 |
| A(3) | modified 1/3 of: 10% sucrose, 10% sorbitol, 1% monosodium glutamate, 2% PVP40, 2.4% glycine; and 20 mM Tris-Acetate pH 6.6 | 6.42 | 555 | 3.97 | 6.68 | 5.46 | 1.22 | n/a | n/a | n/a | n/a | n/a | 11.3 |
| A(4) | 5% Sucrose, 0.5% MSG, 0.5% Urea, 1% BSA, 2.5% PVP, 2.5% glycine in 20 mM Tris-Acetate pH 6.6 | 6.04 | 665 | 2.01 | 6.53 | 5.26 | 1.27 | n/a | n/a | n/a | n/a | -31.4 | 30.0 |
| A(4) | 5% Sucrose with 0.5% MSG, 0.5% Urea, 1% BSA, 2.5% Glycine in 20 mM Tris-Acetate pH 6.6 | 6.18 | 651 | 3.15 | 6.3 | 5.86 | 0.43 | 5.28** | n/a | 5.41** | 5.42** | N/A | 16.2 |
| A(4) | 20 mM Tris-Acetate pH 6.6 with 1% BSA | 2.60 | 6.56 | 755 | 6.36 | 5.17 | 1.14 | n/a | n/a | n/a | N/A | 13.2 | |
| A(4) | 10% sucrose, 10% sorbitol, 1% monosodium glutamate, 2% PVP40, 2.4% glycine, 20 mM Tris Acetate pH 6.6 with 2.5% PEG800 | 0.54 | 6.73 | 773 | n/a | n/a | 1.13 | n/a | n/a | n/a | n/a | -35.8 | 11.3 |
| A(4) | 5% sucrose, 5% sorbitol, 0.5% MSG in 20 mM Tris-Acetate pH 6.6 | 6.65 | 5.18 | n/a | 6.3 | 5.19 | 1.11 | n/a | n/a | n/a | n/a | -43.1 | N/A |
| A(4) | 5% sucrose, 0.5% Urea, 0.5% MSG in 20 mM Trts-Acetate pH 6.6 | 6.60 | 347 | 3.12 | 6.78 | 5.12 | 1.67 | n/a | n/a | n/a | n/a | -40.3 | 24.1 |
| A(4) | 5% sucrose, 0.5% MSG in 20 mM Tris-Acetate pH 6.6 [Control] | 6.61 | 184 | 3.22 | 6.3 | 4.93 | 1.37 | n/a | n/a | n/a | n/a | n/a | 34.1 |
| A(5) | 10% sucrose, 10% sorbitol, 1% monosodium glutamate, 2% PVP40, 2.4% glycine, 20 mM Tris-Acetate pH 6.6 [Control] | 6.37 | 772 | 1.21 | 6.3 | 5.21 | 1.09 | 5.02** | n/a | n/a | n/a | n/a | 15.9 |
| A(5) | 10 mM Histidine, 5% sucrose, 50 mM potassium glutamate, pH 7.0 | 7.01 | 313 | 3.43 | n/a | 5.30 | n/a | 5.37** | n/a | n/a | n/a | n/a | 56.7 |
| A(5) | 10 mM Histidine, 5% sucrose, 50 mM potassium glutamate, pH 7.0, 2.5% Dextran | 7.02 | 293 | 2.16 | 6.12 | 4.63 | 1.49 | 4.99** | n/a | n/a | n/a | -36.6 | 76.9 |
| A(5) | 10 mM Histidine, 5% sucrose, 50 mM potassium glutamate, pH 7.0 | 7.01 | 335 | 3.95 | 6.04 | 4.56 | 1.48 | 4.93** | n/a | n/a | n/a | -38.2 | 48.3 |
| A(5) | 10 mM Histidine, 5% sucrose, 50 mM potassium glutamate, PH7,.0 5% rHSA | 6.79 | 290 | 1.64 | 6.11 | 4.56 | 1.55 | 4.84** | n/a | n/a | n/a | N/A | N/A |
| A(5) | 10% sucrose, 10% sorbitol, 1% monosodium glutamate, 2% PVP40, 2.4% glycine, 10 mM Tris pH 7.4 | 7.19 | 457 | 1.13 | 6.12 | 4.92 | 1.20 | 5.18** | n/a | n/a | n/a | n/a | 22.8 |

TABLE 4-continued

Physical Parameters and Stability Data For Studies A and B

| Study | Composition | pH | Osmolality (mOsm) | Residual Moisture % | Pre-Lyo | Post-Lyo | Δ Lyo titre loss | 4 wk @ 5° C.*; 25° C.; 37° C. | 8 wk @ 5° C.* 25° C.; 37° C. | 12 wk @ −20° C.; 5° C.*; 25° C.; 37° C. | 26 wk @ −20° C.; 5° C.*, and 25° C. | Tg' (° C.) | Tg (° C.) |
|---|---|---|---|---|---|---|---|---|---|---|---|---|---|
| A(5) | 10% sucrose, 10% sorbitol, 1% monosodium glutamate, 2% PVP40, 2.4% glycine, 1% BSA, 20 mM Tris Acetate, pH 6.6 | 6.56 | 755 | 2.60 | 6.36 | 5.17 | 1.19 | 5.14** | n/a | n/a | n/a | n/a | 13.2 |
| A(5) | 10 mM Tris pH 7.4 with 1% BSA | 7.07 | 443 | 1.10 | 6.34 | 5.5 | 0.84 | 5.51** | 5.27 | 5.37 | 5.39 | n/a | 25.9 |
| A(5) | 5% sucrose, 0.5% MSG, 5% BSA/20 mM Tris Acetate pH 6.6 | 6.87 | 287 | 1.15 | 6.23 | 5.44 | 0.79 | 5.46** | n/a | n/a | n/a | −27.1 | 41.4 |
| A(5) | 5% sucrose, 0.5% MSG, 5% rHSA/10 mM Tris pH 7.4 | 6.61 | 290 | 0.62 | 6.08 | 4.63 | 1.45 | 4.95** | n/a | n/a | n/a | −33.0 | 75.4 |
| B | 5% sucrose, 5% sorbitol, 0.5% monosodium glutamate, 1% PVP40, 1.2% glycine, 20 mM Tris-Acetate pH 6.6 [Control] | 6.26 | N/A | N/A | 6.32 | 5.00 | 1.32 | n/a | n/a | n/a | n/a | n/a | n/a |
| B | 5% sucrose, 5% sorbitol, 0.5% monosodium glutamate, 1% PVP40, 1.2% glycine, 10 mM Tris pH 7.4 | 6.98 | 481 | 3.67 | 6.28 | 5.57 | 0.71 | n/a | n/a | n/a | n/a | n/a | n/a |
| B | 5% Sucrose, 0.5% MSG, 0.5% Urea, 2.5% glycine, 1% rHSA in 20 mM Tris-Acetate pH 6.6 | 6.15 | 640 | 3.71 | 6.07 | 5.59 | 0.48 | n/a | n/a | n/a | n/a | n/a | n/a |
| B | 10 mM Histidine, 5% sucrose, 50 mM potassium glutamate, pH 7.0 (w/o NaCl, 5% rHSA) | 6.66 | 318 | 0.87 | 6.18 | 5.26 | 0.92 | n/a | n/a | n/a | n/a | n/a | n/a |

Legend:
*: Storage at −20° C.;
**: Storage at 2-8° C.;
***: Storage at 25° C.;
****: Storage at 37° C.;
N/A - not available In Studies C, D, and E, the physical parameters and stability of various compositions comprising histidine and sucrose were evaluated. The freeze-drying parameters of Studies D and E were the same as the parameters for Study C (see Table 2) except for (1) in Study D the hold time for the secondary dry was 200 minutes; and (2) in Study E, the ramp rate for steps A, B, and C of the primary dry was 0.2 (° C./min) and the hold time for the primary dry was 420 minutes.

In Studies C, D, and E, the main composition ("C1") included 10 mM Histidine, 10% sucrose, 160 mM NaCl, 50 mM potassium glutamate, pH TO with or without one or more additional pharmaceutically acceptable excipients. Another composition ("C2") included the same ingredients as C1 but in lesser amounts: 5 mM Histidine, 5% sucrose, 80 mM NaCl, 25 mM potassium glutamate, pH 7.0. The physical parameters off the compositions in Studies C, D, and E are shown in Table 5.

TABLE 5

Physical Parameters of Compositions in Studies C, D, and E

| Study | Composition | pH | Osmolality (mOsm) | Residual Moisture % | Tg' (° C.) | Tg (° C.) |
|---|---|---|---|---|---|---|
| C | C1 | 7.05 | 733 | 3.84 | −41.9 | 46.6 |
| C | C2 | 7.03 | 670 | 5.0 | −41.9 | n/a |
| C | 2:1 C1 | 7.02 | 732 | 4.85 | −41.9 | n/a |
| D | C1 | 7.06 | 936* | 4.41 | −41.9 | 22.0 |
| D | C1 + 0.1% EDTA | 7.06 | 698 | 4.58 | −40.9 | 33.3 |
| D | C1 + 2.5% Gelatin | 6.71 | 803 | 3.77 | n/a | 42.3 |
| D | C1 + 2.5% rHSA | 6.82 | 712 | 4.12 | −38.2 | 35.5 |
| E | C1 | 7.0 | 797 | 5.1 | −41.9 | n/a |

TABLE 5-continued

Physical Parameters of Compositions in Studies C, D, and E

| Study | Composition | pH | Osmolality (mOsm) | Residual Moisture % | Tg' (° C.) | Tg (° C.) |
|---|---|---|---|---|---|---|
| E | C1 + 0.5% Urea | 7.0 | 735 | 4.7 | −43.5 | n/a |
| E | C1 + 0.1% Pluronic F68 | 7.0 | 650 | 6.1 | −43.0 | n/a |

*Osmolality above preferred range

The stability data of the compositions in Studies C, D, and E are summarized in Table 6 with the values representing infectious titre (log 10 pfu/mL) which was measured as discussed above.

TABLE 6

Stability Data of Compositions in Studies C, D, and E

| Study | Composition | Pre-Lyo | Post-Lyo | Δ titre loss | Storage Time | −20° C. | 5° C. | 25° C. |
|---|---|---|---|---|---|---|---|---|
| C | C1 | 6.99 | 6.30 | 0.69 | 4 weeks | 6.52 | 6.37 | 6.17 |
| C | C1 | 6.99 | 6.30 | 0.69 | 12 weeks | 6.34 | 6.15 | 5.81 |
| C | C1 | 6.99 | 6.30 | 0.69 | 26 weeks | 6.24 | 6.14 | 5.79 |
| C | C2 | 6.48 | 5.99 | 0.49 | n/a | n/a | n/a | n/a |
| C | 2:1 C1 | 6.67 | 6.16 | 0.51 | n/a | n/a | n/a | n/a |
| D | C1 | 7.11 | 6.58 | 0.53 | 12 weeks | 6.45 | 6.30 | 5.57 |
| D | C1 + 0.1% EDTA | 7.09 | 6.45 | 0.64 | 12 weeks | 6.28 | 6.30 | 5.57 |
| D | C1 + 2.5% Gelatin | 7.21 | 6.71 | 0.49 | 12 weeks | 6.38 | 6.42 | 6.31 |
| D | C1 + 2.5% rHSA | 7.11 | 6.54 | 0.57 | 12 weeks | 6.29 | 6.32 | 5.80 |
| E | C1 | 7.0 | 6.61 | 0.39 | 12 weeks | 6.45 | n/a | n/a |
| E | C1 + 0.5% Urea | 7.04 | 6.42 | 0.62 | 12 weeks | 6.33 | n/a | n/a |
| E | C1 + 0.1% Pluronic F68 | 7.08 | 6.33 | 0.75 | 12 weeks | 6.03 | n/a | n/a |
| E | C1 | 7.0 | 6.61 | 0.39 | 26 weeks | 6.43 | 6.40 | 6.10 |
| E | C1 + 0.5% Urea | 7.04 | 6.42 | 0.62 | 26 weeks | 6.43 | 6.34 | 6.04 |
| E | C1 + 0.1% Pluronic F68 | 7.08 | 6.33 | 0.75 | 26 weeks | 5.19 | 5.94 | 6.17 |

Two freeze-dried compositions were selected for further long-term storage studies. The first composition (C1) included: 10 mM Histidine, 10% sucrose, 160 mM NaCl, 50 mM potassium glutamate, pH 7.0 with or without one or more additional pharmaceutically acceptable excipients. The other composition (C3) included: 20 mM Tris-acetate, 5% sucrose, pH 6.6).

Sample vials were stored at 25° C.±2° C. or −70° C.±2° C. (control) for 3 months (T3M) or 6 months (T6M). Following storage for 3 or 6 months, viral infectious titre was measured using the plaque assay (as described earlier). Composition components and results obtained are set out in Table 7.

more than about 20%. Following 3 months and 6 months of storage at 25° C.±2° C., no significant decrease in viral activity was seen in the C1 compositions comprising histidine and sucrose. A significant decrease in viral activity could also be considered an infectious titre that is not within 0.5 $\text{Log}_{10}$ pfu/mL of the titre of the composition measured after lyophilization. Using this standard, the C1 composition did not have a significant decrease in viral activity following storage at 25° C.±2° C. for 3 or 6 months. Adding urea and gelatin to the C1 compositions increased overall stability during long-term storage. Compositions formulated with histidine and a sugar had an overall more optimal long-term stability (including higher titre retention) as compared to compositions formulated without histidine. Although compositions formulated with 20 mM TRIS acetate, 5% sucrose, 0.5% MSG, 1% rHSA, 0.5% Urea and 2.5% Glycine pH 6.6 had minimal titre loss when subjected to freeze-drying,

TABLE 7

| | | Infectious Titre (log10 pfu/mL) | | | | | |
|---|---|---|---|---|---|---|---|
| Composition | Sample # | Pre-Lyo | Post-Lyo (T0) | T3M | T6M | ΔT (loss) | Δ % activity |
| C3 (at −70° C.) | F1 (10-199-1) | n/a | (5.11) | 5.08 | 5.05 | 0.0 | 1% |
| C3 (at 25° C.) | F2 (10-185) | n/a | 5.08 | 2.26 | n/a | 2.8 | 66% |
| C1 (at 25° C.) | F10 (11-156-1) | 6.99 | 6.30 | 5.81 | 5.79 | 0.5 | 8% |
| C1 + EDTA (at 25° C.) | F7 (11-180-2) | 7.09 | 6.45 | 5.57 | | 0.9 | 14% |
| C1 + Gelatin (at 25° C.) | F8 (11-180-3) | 7.21 | 6.71 | 6.31 | | 0.4 | 6% |
| C1 + rHSA (at 25° C.) | F9 (11-180-4) | 7.11 | 6.54 | 5.8 | | 0.7 | 11% |
| C1 + Urea (at 25° C.) | F16 (11-191-2) | 7.04 | 6.42 | | 6.04 | 0.4 | 9% |
| C1 + Pluronic 68 (at 25° C.) | F17 (11-191-3) | 7.08 | 6.33 | | 5.17 | 1.2 | 18% |

For all of the compositions under the tested conditions, the pH remained stable between ±0.5 units.

A significant decrease in viral activity was considered a drop in activity of more than about 10% or in some cases long-term storage of those compositions and storage at ambient temperatures (e.g., 25° C.±2° C.) resulted in titre losses that were higher than those seen in many of the histidine and sugar containing compositions. Moreover, compositions formulated with histidine and sugar met the criteria of preferred attributes.

The addition of certain pharmaceutically acceptable excipients to the histidine containing compositions reduced titre loss. For example, gelatin preserved viral titre during the freeze-drying process and the addition of urea and gelatin to the C1 compositions increased overall stability during long-term storage.

In regards to the cycle parameters utilized during the freeze-drying process, a lower primary dry ramp rate and a reduced secondary dry shelf temperature and ramp rate minimized titre loss.

Example 3

A freeze-thaw study was designed to test the stability of the C1 composition (HSV-529 in 10 mM Histidine, 10% sucrose, 160 mM NaCl, 50 mM potassium glutamate, pH 7.0) when exposed to freeze-thaw stress. In one test, 0.7 mL of different lots of the C1 composition was placed into a 3 mL Type I glass vial and stored at either below −60° C. or −20° C. Following storage for different amounts of time, the compositions were thawed at 37° C. in a water bath, and viral infectious titre was measured using the plaque assay (as described earlier). The results obtained are set forth in Table 8 (below −60° C.) and Table 9 (−20° C.).

TABLE 8

(Plaque Assay Following Storage at Below −60° C.)

| | | Infectious Titre ($Log_{10}$ pfu/mL) | | | | | | | |
|---|---|---|---|---|---|---|---|---|---|
| Composition | Sample # | 0 | 1 wk | 2 wk | 4 wk | 8 wk | 12 wk | 26 wk | 38 wk |
| C1 | Lot A (11-150) | 7.25 | 7.3 | | 7.33 | 7.34 | 7.11 | 7.18 | 7.14 |
| C1 | Lot B (11-183) | 7.08 | | 6.91 | 6.92 | 6.88 | 6.98 | 7 | |
| C1 | Lot C (11-234) | 6.82 | | 7 | 7.09 | 6.93 | 6.85 | | |

TABLE 9

(Plaque Assay Following Storage at −20° C.)

| | | Infectious Titre ($Log_{10}$ pfu/mL) | | | | | | |
|---|---|---|---|---|---|---|---|---|
| Composition | Sample # | 0 | 1 wk | 2 wk | 4 wk | 8 wk | 12 wk | 26 wk |
| C1 | Lot A (11-150) | 7.25 | 7.07 | 7.02 | 7.18 | | | |
| C1 | Lot B (11-183) | 6.91 | 6.71 | 6.64 | 6.68 | 6.55 | 6.5 | 6.18 |
| C1 | Lot C (11-234) | 6.82 | | 6.84 | 6.86 | 6.73 | 6.57 | |

Following storage at below −60° C., the HSV-2 in the C1 composition, maintained an infectious titre higher than 6.5 ($Log_{10}$ pfu/mL) for up to 38 weeks, with a titre loss of less than about 0.1 $Log_{10}$ pfu/mL, Following storage at −20° C., the HSV-2 in the C1 composition, maintained an infectious titre higher than 6.5 ($Log_{10}$ pfu/mL) for up to 8-12 weeks, with a titre loss less than 0.3 $Log_{10}$ pfu/mL for at least 4 weeks, and, in some instances, up to 12 weeks.

In a separate study, larger volumes (25 mL in 200-L NALGENE® bottle) of the C1 composition containing HSV-529 were subjected to freeze-thaw stress. Samples were frozen overnight at below −60° C. and thawed in a 37° C. water bath. The infectious titre of HSV-529 in the C1 compositions was measured using the plaque assay, as discussed previously, following multiple freeze-thaw cycles. The results are shown in Table 10, with the C1 composition maintaining a high viral titre and a viral titre loss of less than 0.2 Log 10 pfu/mL following at least 3 freeze-thaw cycles.

TABLE 10

(Multiple Freeze-Thaw Cycles)

| | | Infectious Titre (log10 pfu/mL) | | | |
|---|---|---|---|---|---|
| Composition | Sample# | 0 | Cycle 1 | Cycle 2 | Cycle 3 |
| C1 | Lot A (11-146) | 7.15 | 7.06 | 7.08 | 6.99 |

Example 4

A temperature excursion study was designed to simulate GMP manufacturing conditions and to test stability of HSV-529 compositions when temperature was changed from room temperature (25° C.) to 2-8° C. Two HSV-529 lots were compared: 1) HSV-529 in the C1 composition (10 mM Histidine, 10% sucrose, 160 mM NaCl, 50 mM potassium glutamate, pH 7.0) and 2) HSV-529 in a composition ("C3+MSG") containing 20 mM Tris-acetate, 5% sucrose, 0.5% MSG, pH 6.6). The temperature excursion schedule is set forth in Table 11 and was based on a standard GMP process (wait time to packing and labeling is 4 days) and a worst case scenario (wait time to packing and labeling is 17 days).

TABLE 11

(Temperature Excursion Schedule)

| Step # | 1 | 2 | 3 | 4 |
|---|---|---|---|---|
| Temp | 37° C. | 25° C. | 2-8° C. | 25° C. |
| Duration | | 8 Hrs | 16 Hrs | 8 Hrs |

TABLE 11-continued (Temperature Excursion Schedule)

| Mock GMP process step | Thaw | Directly Filling | | Visual Inspection |
|---|---|---|---|---|
| Step # | 5 | 6 | | 7 | 8 |
| Temp Duration Mock GMP process step | 2-8° C. 16 Hrs | 25° C. 4 Hrs AQL | | 2-8° C. 16 Hrs | 25° C. 4 Hrs Sample labeling |

| Case A: Standard Step 9 = 4 days | | | | |
|---|---|---|---|---|
| Step # | 9 | 10 | 11 | 12 |
| Temp Duration | 2-8° C. 4 days | 25° C. 8 hrs | −70° C. At least overnight | 37° C. |
| Mock GMP process step | Wait time to L/P | Labeling Packing | | 37° C. water bath / Hand Thaw |

| Case B: Worse Case Scenario Step 9 = 17 Days | | | | |
|---|---|---|---|---|
| Step # | 9B | 10B | 11B | 12B |
| Temp Duration | 2-8° C. 17 days | 25° C. 8 hrs | −70° C. At least overnight | 37° C. |
| Mock GMP process step | Wait time to L/P | Labeling Packing | | 37° C. water bath / Hand Thaw |

The infectious titre following standard GMP consitions (Case A) and worst case scenario (Case B) was measured using the plaque assay. The results are shown in Tables 12 and 13.

TABLE 12

(Temperature Excursion Study Case A)

| | | Infectious Titre (log10 pfu/mL) | | | | |
|---|---|---|---|---|---|---|
| Composition | Sample # | 0 | Step 10 | Titre loss (Step 10) | Step 12 | Titre loss (Step 12) |
| C1 | Lot A (11-135) | 7.15 | 6.75 | 0.40 | 6.57 | 0.58 |
| C3 + MSG | Lot B (11-135) | 7.69 | 6.1 | 1.59 | 5.82 | 1.87 |

TABLE 13

(Temperature Excursion Study Case B)

| | | Infectious Titre (log10 pfu/mL) | | | | |
|---|---|---|---|---|---|---|
| Composition | Sample # | 0 | Step 10 | Titre loss (Step 10) | Step 12 | Titre loss (Step 12) |
| C1 | Lot A (11-135) | 7.15 | 6.50 | 0.65 | 6.55 | 0.60 |
| C3 + MSG | Lot B (11-135) | 7.69 | 5.94 | 1.75 | 5.79 | 1.90 |

HSV-529 formulated in C1 resulted in much lower titre loss than HSV-529 formulated in C3+MSG in both the Case A and Case B temperature excursion studies.

Example 5

Assays were also run to compare the stability of liquid HSV-529 compositions following storage at different temperatures. As above, two compositions were tested, C1 (HSV-529 in 10 mM Histidine, 10% sucrose, 160 mM NaCl, 50 mM potassium glutamate, pH 7.0) and C3+MSG (HSV-529 in 20 mM Tris-acetate, 5% sucrose, 0.5% MSG, pH 6.6). Stability was measured by the plaque assay, as above. The results of the liquid formulation stability assay are set forth in Table 14.

TABLE 14

(Liquid Stability at Different Temperatures)

| | | Infectious Titre (log10 pfu/mL) | | | | |
|---|---|---|---|---|---|---|
| Composition | Temp. | 0 | 1 wk | Titre loss (1 wk) | 2 wk | Titre loss (2 wk) |
| C1 | 2-8° C. | 7.15 | 6.97 | 0.18 | 6.86 | 0.29 |
| C3 + MSG | 2-8° C. | 7.15 | | | 6.61 | 0.54 |
| C1 | 25° C. | 6.13 | 5.8 | 0.33 | 5.68 | 0.45 |
| C3 + MSG | 25° C. | 6.13 | 5.69 | 0.44 | 5.59 | 0.54 |

The histidine formulation (C1) was more stable than the Tris-acetate composition (C3+MSG) at both 25° C. and 2-8° C. The histidine formulation stored at 2-8° C. for at least 2 weeks had a viral titre loss of less than 0.3 $Log_{10}$ pfu/mL.

To investigate the initial titre drop, a modified liquid stability assay was designed. C1 (HSV-529 in 10 mM Histidine, 10% sucrose, 160 mM NaCl, 50 mM potassium glutamate, pH 7.0) was stored at both 25° C. and 2-8° C. for increasing lengths of time. At the end of the time period, the samples were immediately frozen to below −60° C. The samples were thawed in a 37° C. water bath and tested for infectious titre using the plaque assay. The results of this liquid stability assay are presented in Table 15.

TABLE 15

(Modified Liquid Stability Assay)

| | | Infectious Titre ($Log_{10}$ pfu/mL) | | | | | | | | | |
|---|---|---|---|---|---|---|---|---|---|---|---|
| Composition | Temp | 0 | 1 h | 2 h | 4 h | 6 h | 24 h | 30 h | 2 d | 3 d | 6 d |
| C1 | 2-8° C. | 6.87 | 6.86 | 6.88 | 6.89 | 6.83 | 6.74 | 6.66 | 6.66 | 6.63 | 6.54 |
| C1 | 25° C. | 6.87 | 6.81 | 6.76 | 6.77 | 6.74 | 6.51 | 6.51 | 6.54 | 6.46 | 6.19 |

In this study, the HSV-529 in the C1 composition had a titre loss of less than 0.3 $\text{Log}_{10}$ pfu/mL for at least 3 days when stored at 2-8° C. and for at least 6 hours when stored at 25° C.

Longer-term stability of the liquid C1 composition was also evaluated. 0.7 mL of different lots of the C1 composition was placed into a 3 mL Type I glass vial and stored at 2-8° C. or 23-27° C. for different amounts of time. The results obtained are set forth in Table 16 (2-8° C.) and Table 17 (23-27° C.).

TABLE 16

(Liquid Stability Following Storage at 2-8° C.)

| | | Infectious Titre ($\text{Log}_{10}$ pfu/mL) | | | | | | | |
|---|---|---|---|---|---|---|---|---|---|
| Composition | Sample # | 0 | 1 wk | 2 wk | 4 wk | 8 wk | 12 wk | 26 wk | 38 wk |
| C1 | Lot A (11-150) | 7.25 | 6.98 | | 6.86 | 6.68 | 6.32 | 6.12 | 5.99 |
| C1 | Lot B (11-183) | 6.91 | 6.69 | 6.61 | 6.59 | 6.41 | 6.33 | 5.96 | |
| C1 | Lot C (11-234) | 6.82 | | 6.29 | 6.21 | 5.85 | 5.53 | | |

TABLE 17

(Liquid Stability Following Storage at 23-27° C.)

| | | Infectious Titre ($\text{Log}_{10}$ pfu/mL) | | | | | |
|---|---|---|---|---|---|---|---|
| Composition | Sample # | 0 | 1 wk | 2 wk | 4 wk | 8 wk | 12 wk |
| C1 | Lot A (11-150) | 7.25 | 6.75 | 6.72 | 6.32 | 5.64 | |
| C1 | Lot B (11-183) | 6.91 | 6.51 | 6.35 | 6.11 | 5.32 | 4.33 |
| C1 | Lot C (11-234) | 6.82 | | 5.78 | 5.73 | 4.77 | 4.31 |

Following storage at 2-8° C., the HSV-2 in the C1 composition maintained an infectious titre higher than 6.5 ($\text{Log}_{10}$ pfu/mL) for up to 2-8 weeks, depending on the lot and the starting viral titre. Following storage at 23-27° C., the HSV-2 in the C1 composition maintained an infectious titre higher than 6.5 ($\text{Log}_{10}$ pfu/mL) for up to 1-2 weeks, depending on the lot and the starting viral titre. In addition, depending on the lot, the HSV-2 in the C1 composition had a titre loss of less than 0.3 $\text{Log}_{10}$ pfu/mL following 1 week, or, in one instance, even 2 weeks, of storage at 2-8° C.

Although preferred embodiments have been described herein, it is understood that variations and modifications are contemplated and are readily apparent to those skilled in the art.

It must also be noted that, as used in this disclosure and the appended claims, the singular forms "a" "an", and "the" include plural referents unless the context clearly dictates otherwise. Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination). Ranges may be expressed herein as from about one particular value, and/or to about another particular value. When such a range is expressed, another aspect includes from the one particular value and/or to the other particular value. Similarly, when values are expressed as approximations, by use of the antecedent about, it will be understood that the particular value forms another aspect. It will be further understood that the endpoints of each of the ranges are significant both in relation to the other endpoint, and independently of the other endpoint. All references cited in this disclosure are hereby incorporated herein in their entirety.

What is claimed is:

1. A method of manufacturing a dried composition comprising a live, attenuated or genetically modified herpesvirus, the method comprising:
   (i) admixing the live, attenuated or genetically modified herpesvirus with histidine or glutamine and sucrose or trehalose; and
   (ii) drying the admixture, to form a dried composition, wherein the dried composition consists of:
   a live, attenuated or genetically modified herpes simplex virus type-2 (HSV-2) or herpes simplex virus type-1 (HSV-1),
   1 mM to 50 mM histidine or glutamine,
   sucrose or trehalose,
   sodium chloride, and
   glutamate, and has a pH of about 6.5 to 7.5.

2. The method of claim 1, wherein the admixture is dried by means of a method selected from the group consisting of freeze-drying, foam-drying, and spray-drying.

3. The method of claim 1, wherein the HSV-2 or the HSV-1 is a replication-defective herpes simplex virus.

4. The method of claim 1, wherein viral titres of the live, attenuated or genetically modified herpesvirus are between $10^7$ to $10^5$ pfu/mL before drying.

5. The method of claim 1, wherein the glutamate is selected from the group consisting of potassium glutamate, mono sodium glutamate, and sodium glutamate.

6. The method of claim 1, wherein the glutamate is present in an amount of 1 mM to 100 mM.

7. The method of claim 1, wherein the histidine is present in an amount of 5 mM to 20 mM and the sucrose is present in an amount of 5% to 10% w/v.

8. The method of claim 1, wherein the glutamate is selected from the group consisting of 1 mM to 100 mM potassium glutamate, 1 mM to 100 mM mono sodium glutamate, and 1 mM to 100 mM sodium glutamate.

9. The method of claim 1, wherein the live, attenuated or genetically modified herpesvirus is a HSV-2.

10. The method of claim 9, wherein the HSV-2 is a replication defective HSV-529 strain.

11. The method of claim 1, wherein the HSV-1 or HSV-2 contains less than 10 ng of host cell DNA per $1 \times 10^7$ pfu/mL.

12. The method of claim 1, wherein the residual moisture content of the dried composition is 6% or less.

13. The method of claim 1, wherein the histidine is present in an amount of 5 mM to 20 mM histidine, the sucrose is present in an amount of 5% to 10% w/v, and the glutamate comprises potassium glutamate and the potassium glutamate is present in an amount of 25 mM to 75 mM.

14. The method of claim 13, wherein the sodium chloride is present in an amount of 80 to 160 mM.

15. The method of claim 1, wherein the sodium chloride is present in an amount of 10 to 200 mM.

16. A method of manufacturing a dried composition comprising a live, attenuated or genetically modified herpesvirus, the method comprising:
- (i) admixing the live, attenuated or genetically modified herpesvirus with histidine, sucrose or trehalose, sodium chloride, and glutamate; and
- (ii) drying the admixture, wherein the dried composition consists of:
- a live, attenuated or genetically modified herpes simplex virus type-2 (HSV-2) or herpes simplex virus type-1 (HSV-1),
- about 10 mM 1 mM,
- about 10% w/v sucrose or trehalose, sodium chloride, and
- about 50 mM glutamate, and has a pH of about 6.5 to 7.5.

* * * * *

UNITED STATES PATENT AND TRADEMARK OFFICE
CERTIFICATE OF CORRECTION

PATENT NO.         : 12,214,035 B2
APPLICATION NO.    : 17/576021
DATED              : February 4, 2025
INVENTOR(S)        : Stephen Anderson et al.

Page 1 of 1

It is certified that error appears in the above-identified patent and that said Letters Patent is hereby corrected as shown below:

In the Claims

Column 25, Line 23: "about 10 mM 1 mM" should be -- about 10 mM histidine --.

Signed and Sealed this
Eighteenth Day of March, 2025

Coke Morgan Stewart
*Acting Director of the United States Patent and Trademark Office*